(12) United States Patent
Hagiya et al.

(10) Patent No.: US 8,350,091 B2
(45) Date of Patent: *Jan. 8, 2013

(54) POTASSIUM FLUORIDE DISPERSION AND PROCESS FOR PRODUCING FLUORINE-CONTAINING ORGANIC COMPOUND USING THE SAME

(75) Inventors: Koji Hagiya, Ibaraki (JP); Kazuaki Sasaki, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/341,069

(22) Filed: Dec. 30, 2011

(65) Prior Publication Data

US 2012/0097891 A1    Apr. 26, 2012

Related U.S. Application Data

(62) Division of application No. 12/298,539, filed as application No. PCT/JP2007/059439 on Apr. 26, 2007.

(30) Foreign Application Priority Data

Apr. 27, 2006  (JP) ................................. 2006-123126
Jul. 6, 2006  (JP) ................................. 2006-186334

(51) Int. Cl.
    *C07C 45/90* (2006.01)
(52) U.S. Cl. ........ 568/433; 568/437; 568/814; 568/937; 568/938; 560/83
(58) Field of Classification Search ........................ None
See application file for complete search history.

(56) References Cited

U.S. PATENT DOCUMENTS

| | | | |
|---|---|---|---|
| 4,069,262 A | 1/1978 | Kunz | |
| 4,642,398 A * | 2/1987 | Cantrell | 568/937 |
| 4,713,231 A | 12/1987 | Campbell et al. | |
| 4,849,552 A | 7/1989 | Cantrell | |
| 6,127,581 A | 10/2000 | Wiedemann et al. | |
| 6,241,917 B1 | 6/2001 | Owens et al. | |
| 8,017,798 B2 | 9/2011 | Hagiya | |
| 8,039,680 B2 | 10/2011 | Hagiya | |
| 2011/0112321 A1 | 5/2011 | Hagiya | |

FOREIGN PATENT DOCUMENTS

| | | |
|---|---|---|
| EP | 0 140 482 | 5/1985 |
| JP | 58-157727 | 9/1983 |
| JP | 58-199715 | 11/1983 |
| JP | 61-050945 | 3/1986 |
| JP | 63-010737 | 1/1988 |
| JP | 63-089417 | 4/1988 |
| JP | 63-502181 | 8/1988 |
| JP | 2-11571 | 3/1990 |
| JP | 02-111624 | 4/1990 |
| JP | 04-006104 | 1/1992 |
| JP | 2000-86553 | 3/2000 |
| WO | WO 87/04151 | 7/1987 |

OTHER PUBLICATIONS

Supplementary European Search Report dated Jul. 20, 2010, in European Application No. 07742874.6-1270.
Chinese Office Action dated Apr. 21, 2010, in Chinese Application No. 200780014733.9.
European Office Action dated Jun. 27, 2011, in European Application No. 07742874.6-1270.
International Search Report dated Aug. 21, 2007, in International Application No. PCT/JP2007/059439.
T. Smyth, et al., "Inexpensive, Active KF for Nucleophilic Aromatic Displacement Reactions.", Tetrahedron, vol. 51, No. 22, 1995, pp. 6363-6376.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

A potassium fluoride dispersion essentially consisting of potassium fluoride and an aprotic organic solvent having a boiling point higher than that of methanol, which is obtainable by mixing a mixture containing potassium fluoride and 5 to 50 parts by weight of methanol per 1 part by weight of potassium fluoride with the aprotic organic solvent followed by concentrating the obtained mixture, and a process for producing a fluorine-containing organic compound comprising contacting an organic compound having at least one group capable of being substituted nucleophilically with a fluorine atom with the potassium fluoride dispersion.

8 Claims, 10 Drawing Sheets particle diameter (μm)

POTASSIUM FLUORIDE DISPERSION AND PROCESS FOR PRODUCING FLUORINE-CONTAINING ORGANIC COMPOUND USING THE SAME

This application is a Divisional of U.S. application Ser. No. 12/298,539, filed on Oct. 27, 2008, which is the National Stage of PCT/JP2007/059436, filed on Apr. 26, 2007.

TECHNICAL FIELD

The present invention relates to a potassium fluoride dispersion and a process for producing a fluorine-containing organic compound using the same.

BACKGROUND ART

Potassium fluoride is useful as a fluorinating agent for an organic compound. WP1987/004151 discloses that a method comprising preparing a potassium fluoride dispersion by mixing potassium fluoride with about 1.4 parts by weight of methanol per 1 parts by weight of potassium fluoride and sulfolane followed by concentrating methanol from the obtained mixture, and fluorinating an organic compound using the prepared potassium fluoride dispersion. However, an activity of the potassium fluoride dispersion in a fluorination reaction is not necessarily enough and it is necessary to conduct a fluorination reaction using an expensive phase transfer catalyst.

DISCLOSURE OF THE INVENTION

The present invention is to provide

<1> A potassium fluoride dispersion essentially consisting of potassium fluoride and an aprotic organic solvent having a boiling point higher than that of methanol, which is obtainable by mixing a mixture containing potassium fluoride and 5 to 50 parts by weight of methanol per 1 part by weight of potassium fluoride with the aprotic organic solvent followed by concentrating the obtained mixture;

<2> The potassium fluoride dispersion according to <1>, wherein the mixture containing potassium fluoride and 5 to 50 parts by weight of methanol per 1 part by weight of potassium fluoride is a solution wherein potassium fluoride is dissolved perfectly in methanol;

<3> The potassium fluoride dispersion according to <2>, wherein potassium fluoride in the potassium fluoride dispersion is potassium fluoride wherein a part of or all of the initial particles, of which particle diameter is 0.1 to 5 μm, are flocculated to form particles having 5 to 25 μm of volumetric average particle diameter;

<4> A process for producing a potassium fluoride dispersion essentially consisting of potassium fluoride and an aprotic organic solvent having a boiling point higher than that of methanol, which comprises mixing a mixture containing potassium fluoride and 5 to 50 parts by weight of methanol per 1 part by weight of potassium fluoride with the aprotic organic solvent followed by concentrating the obtained mixture;

<5> The method according to <4>, wherein the mixture containing potassium fluoride and 5 to 50 parts by weight of methanol per 1 part by weight of potassium fluoride is a solution wherein potassium fluoride is dissolved perfectly in methanol;

<6> The method according to <4>, wherein the concentration is conducted while adding the mixture containing potassium fluoride and 5 to 50 parts by weight of methanol per 1 part by weight of potassium fluoride into the aprotic organic solvent having a boiling point higher than that of methanol, which is adjusted at a temperature which is the boiling point of methanol or more;

<7> The method according to any one of <4> to <6>, wherein the aprotic organic solvent is an aprotic polar solvent;

<8> The method according to <7>, wherein the aprotic polar solvent is a sulfone solvent or a sulfoxide solvent;

<9> The method according to <4>, wherein the mixture containing potassium fluoride and 5 to 50 parts by weight of methanol per 1 part by weight of potassium fluoride is a mixture obtainable by mixing hydrogen fluoride with potassium hydroxidein methanol;

<10> The method according to <9>, wherein hydrogen fluoride is hydrofluoric acid;

<11> The method according to <5>, wherein potassium fluoride in the potassium fluoride dispersion is potassium fluoride wherein apart of or all of the initial particles, of which particle diameter is 0.1 to 5 μm, are flocculated to form particles having 5 to 25 μm of volumetric average particle diameter;

<12> A process for producing a fluorine-containing organic compound comprising contacting an organic compound having at least one group capable of being substituted nucleophilically with a fluorine atom with the potassium fluoride dispersion according to any one of <1> to <3>;

<13> The process according to <12>, wherein the group capable of being substituted nucleophilically with a fluorine atom is a chlorine atom, a bromine atom, an iodine atom, a nitro group, a sulfo group, an optionally substituted alkylsulfonyloxy group, an optionally substituted arylsulfonyloxy group or an optionally substituted acyloxy group;

<14> The process according to <12>, wherein the organic compound having at least one group capable of being substituted nucleophilically with a fluorine atom is a compound wherein at least one hydrogen atom of an optionally substituted aliphatic hydrocarbon compound is substituted with a group capable of being substituted nucleophilically with a fluorine atom;

<15> The process according to <12>, wherein the organic compound having at least one group capable of being substituted nucleophilically with a fluorine atom is a compound wherein at least one hydrogen atom of an optionally substituted aromatic hydrocarbon compound is substituted with a group capable of being substituted nucleophilically with a fluorine atom;

<16> The process according to <12>, wherein the organic compound having at least one group capable of being substituted nucleophilically with a fluorine atom is a compound wherein at least one hydrogen atom of an optionally substituted heteroaromatic hydrocarbon compound is substituted with a group capable of being substituted nucleophilically with a fluorine atom;

<17> The process according to <15>, wherein the compound wherein at least one hydrogen atom of an optionally substituted aromatic hydrocarbon compound is substituted with a group capable of being substituted nucleophilically with a fluorine atom is tetrachloroterephthalic dichloride, and the fluorine-containing organic compound is tetrafluoroterephthalic difluoride;

<18> The process according to <15>, wherein the compound wherein at least one hydrogen atom of an optionally substituted aromatic hydrocarbon compound is substituted with a group capable of being substituted nucleophilically with a fluorine atom is 2,4-dichloronitrobenzene, and the fluorine-containing organic compound is 2,4-difluoronitrobenzene;

<19> The process according to <15>, wherein the compound wherein at least one hydrogen atom of an optionally substituted aromatic hydrocarbon compound is substituted with a group capable of being substituted nucleophilically with a fluorine atom is 4-chloronitrobenzene, and the fluorine-containing organic compound is 4-fluoronitrobenzene;

<20> The process according to <16>, wherein the compound wherein at least one hydrogen atom of an optionally substituted heteroaromatic hydrocarbon compound is substituted with a group capable of being substituted nucleophilically with a fluorine atom is 4,5,6-trichloropyrimidine, and the fluorine-containing organic compound is 4,5,6-trifluoropyrimidine;

<21> The process according to <14>, wherein the compound wherein at least one hydrogen atom of an optionally substituted aliphatic hydrocarbon compound is substituted with a group capable of being substituted nucleophilically with a fluorine atom is benzyl bromide, and the fluorine-containing organic compound is benzyl fluoride;

<22> Use of the potassium fluoride dispersion according to any one of <1> to <3> for fluorination of an organic compound having at least one group capable of being substituted nucleophilically with a fluorine atom;

<23> Use of the potassium fluoride dispersion obtained according to any one of <4> to <11> for fluorination of an organic compound having at least one group capable of being substituted nucleophilically with a fluorine atom;

<24> A method for fluorinating an organic compound comprising contacting an organic compound having at least one group capable of being substituted nucleophilically with a fluorine atom with the potassium fluoride dispersion according to any one of <1> to <3>;

<25> A method for fluorinating an organic compound comprising contacting an organic compound having at least one group capable of being substituted nucleophilically with a fluorine atom with the potassium fluoride dispersion obtained according to any one of <4> to <11>.

BEST MODE FOR CARRYING OUT THE PRESENT INVENTION

Figure 1:
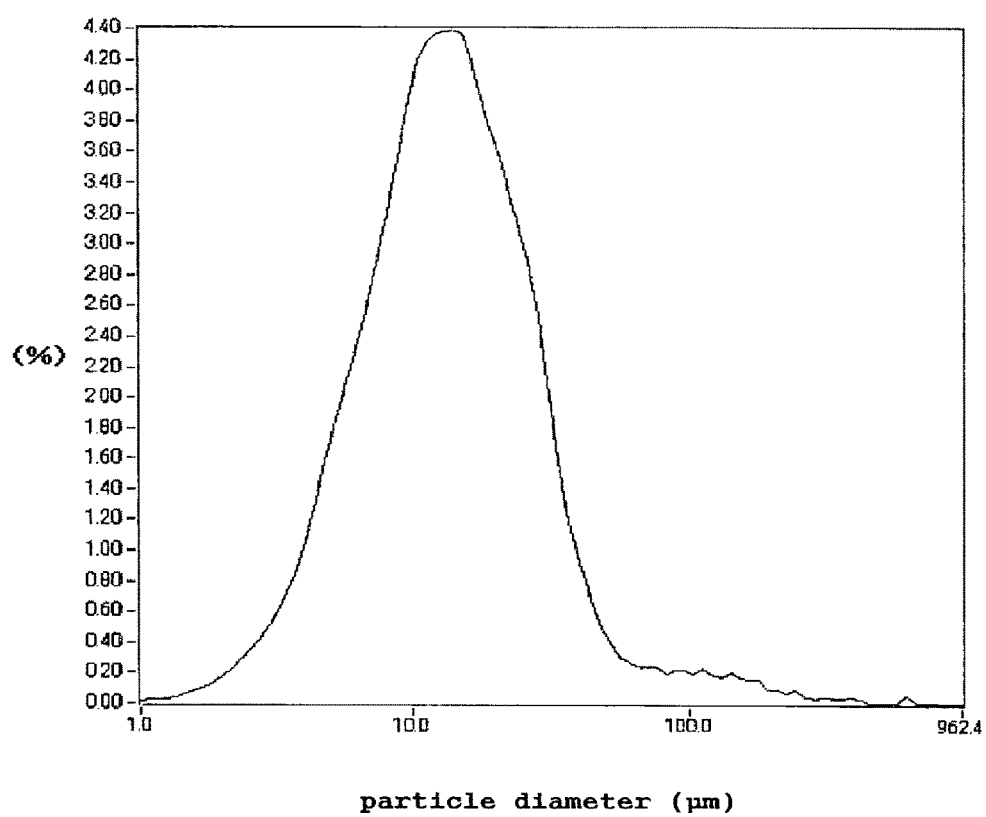
FIG. 1 This is a drawing showing volumetric particle size distribution of the potassium fluoride dispersion obtained in Example 14.

The potassium fluoride dispersion of the present invention is a potassium fluoride dispersion obtainable by mixing a mixture containing potassium fluoride and 5 to 50 parts by weight of methanol per 1 part by weight of potassium fluoride with an aprotic organic solvent having a boiling point higher than that of methanol followed by concentrating the obtained mixture, and it essentially consists of potassium fluoride and the aprotic organic solvent having a boiling point higher than that of methanol.

A commercially available methanol may be used and one produced by reacting potassium hydroxide with hydrogen fluoride may be used. It may be an anhydride or a hydrate. Alternatively, a hydrous one may be used.

From the economic viewpoint, one produced by reacting potassium hydroxide with hydrogen fluoride is preferably used as potassium fluoride. A commercially available potassium hydroxide is usually used. An aqueous solution of potassium hydroxide may be used and a solution of an organic solvent of potassium hydroxide may be used. As the organic solvent, an alcohol solvent is preferable and methanol is more preferable. An organic solvent containing water may be used. A commercially available hydrogen fluoride is usually used. Hydrogen fluoride gas may be used and hydrofluoric acid may be used. The amount of hydrogen fluoride to be used is usually 0.9 to 1.1 moles and preferably 0.99 to 1.01 moles per 1 mole of potassium hydroxide.

The reaction of hydrogen fluoride and potassium hydroxide is usually conducted in an organic solvent, and an alcohol solvent is preferable as the organic solvent and methanol is more preferable.

Potassium fluoride can be isolated by a concentration of the reaction mixture obtained by reacting hydrogen fluoride with potassium hydroxide. When the above-mentioned reaction mixture does not contain any organic solvent other than methanol, the obtained reaction mixture may be used as it is for producing the potassium fluoride dispersion.

When the reaction mixture containing potassium fluoride, which is obtained by reacting hydrogen fluoride with potassium hydroxide in methanol, is used as potassium fluoride for a preparation of the potassium fluoride dispersion, the amount of methanol to be used may be decided so that the amount of methanol will become 5 to 50 parts by weight per 1 part of potassium fluoride generated in the reaction.

As the mixture containing potassium fluoride and 5 to 50 parts by weight of methanol per 1 part by weight of potassium fluoride, a solution wherein potassium fluoride is dissolved perfectly in methanol is preferable. Depending on the preparing temperature of the solution, 8 to 50 parts by weight of methanol per 1 part of potassium fluoride is more preferably used in the point of easy preparation of the solution.

The mixture containing potassium fluoride and 5 to 50 parts by weight of methanol per 1 part by weight of potassium fluoride is usually prepared by mixing potassium fluoride with the pre-determined amount of methanol. The preparing temperature is usually 0 to 100° C. and preferably 20 to 70° C.

The aprotic organic solvent having a boiling point higher than that of methanol may be a nonpolar solvent or a polar solvent. An aprotic polar solvent is preferable.

Examples of the aprotic polar solvent having a boiling point higher than that of methanol include ether solvents such as diisopropyl ether, dibutyl ether, dioxane, diethylene glycol dimethyl ether and triethylene glycol dimethyl ether; sulfone solvents such as sulfolane, dimethylsulfone and methyl ethyl sulfone; sulfoxide solvents such as dimethylsulfoxide, diethylsulfoxide and tetramethylenesulfoxide; amide solvents such as N,N-dimethylformamide, N,N-dimethylacetamide and N-methylpyrolidone; and nitrile solvents such as butyronitrile and adiponitrile. Sulfone solvents, sulfoxide solvents and amide solvents are preferable, and sulfone solvents and sulfoxide solvents are more preferable.

Examples of the aprotic nonpolar solvent having a boiling point higher than that of methanol include aliphatic hydrocarbon solvents such as hexane, heptane, octane and cyclohexane; and aromatic hydrocarbon solvents such as benzene, toluene and xylene.

The aprotic organic solvent may be used alone, and two or more thereof may be mixed to use.

The amount of the aprotic organic solvent having a boiling point higher than that of methanol to be used may be usually 1 part by weight or more per 1 part by weight of potassium fluoride. While there is no upper limit particularly, since the volume efficiency goes down when the amount thereof is too much, practical amount thereof is 20 parts by weight or less.

The potassium fluoride dispersion of the present invention can be produced by mixing a mixture containing potassium fluoride and 5 to 50 parts by weight of methanol per 1 part by weight of potassium fluoride with an aprotic organic solvent having a boiling point higher than that of methanol followed by concentrating the obtained mixture. In order for the easy removal of methanol in the mixture containing potassium fluoride and 5 to 50 parts by weight of methanol per 1 part by weight of potassium fluoride, a solvent capable of forming an azeotrope with methanol may be used together. Alternatively, the concentration may be conducted while adding the mixture containing potassium fluoride and 5 to 50 parts by weight of methanol per 1 part by weight of potassium fluoride into the aprotic organic solvent adjusted at a temperature which is the boiling point of methanol or more. Preferably, the concentration is conducted while adding the mixture containing potassium fluoride and 5 to 50 parts by weight of methanol per 1 part by weight of potassium fluoride into the aprotic organic solvent adjusted at a temperature which is the boiling point of methanol or more to prepare the potassium fluoride dispersion.

Examples of the solvent capable of forming an azeotrope with methanol include aromatic hydrocarbon solvents such as benzene, toluene and xylene; and aliphatic hydrocarbon solvents such as hexane and cyclohexane.

The operation pressure on concentrating is usually 0.7 to 200 kPa and concentrating temperature is usually 20 to 200° C.

The concentration is carried out until the potassium fluoride dispersion essentially consisting of potassium fluoride and the aprotic organic solvent having a boiling point higher than that of methanol can be obtained.

The potassium fluoride dispersion thus obtained essentially consists of potassium fluoride and the aprotic organic solvent having a boiling point higher than that of methanol, and it is a mixture wherein the fine powder of potassium fluoride is dispersed in the aprotic organic solvent. The content of potassium fluoride in the potassium fluoride dispersion is usually 5 to 70% by weight.

Especially, potassium fluoride in the potassium fluoride dispersion prepared by using the solution wherein potassium fluoride is dissolved perfectly in methanol has 0.1 to 5 μm of particle diameter of the initial particles and a part or all of the initial particles are flocculated to form particles having 5 to 25 μm of volumetric average particle diameter.

The potassium fluoride dispersion thus obtained has a high activity in a fluorination reaction.

Next, a process for producing a fluorine-containing organic compound comprising contacting an organic compound having at least one group capable of being substituted nucleophilically with a fluorine atom (hereinafter, simply referred to as the organic compound) with the potassium fluoride dispersion of the present invention will be illustrated.

Examples of the group capable of being substituted nucleophilically with a fluorine atom include a chlorine atom, a bromine atom, an iodine atom, a nitro group, a sulfo group, an optionally substituted alkylsulfonyloxy group, an optionally substituted arylsulfonyloxy group and an optionally substituted acyloxy group. When the organic compound has two or more groups capable of being substituted nucleophilically with a fluorine atom, they may be same or different from each other.

Examples of the optionally substituted alkylsulfonyloxy group include an alkylsulfonyloxy group which may be substituted with a fluorine atom or atoms such as a methanesulfonyloxy group, an ethanesulfonyloxy group and a trifluoromethanesulfonyloxy group. Examples of the optionally substituted arylsulfonyloxy group include a p-toluenesulfonyloxy group, a benzenesulfonyloxyl group and a 1-naphthalenesulfonyloxy group. Examples of the optionally substituted acyloxy group include an acyloxy group which may be substituted with a fluorine atom or atoms such as a trifluoroacetoxy group, a pentafluoroethylcarbonyloxy group, a tetrafluorobenzoyloxy group and a benzoyloxy group.

Examples of the organic compound include a compound wherein at least one hydrogen atom of an optionally substituted aliphatic hydrocarbon compound is substituted with a group capable of being substituted nucleophilically with a fluorine atom, a compound wherein at least one hydrogen atom of an optionally substituted aromatic hydrocarbon compound is substituted with a group capable of being substituted nucleophilically with a fluorine atom, and a compound wherein at least one hydrogen atom of an optionally substituted heteroaromatic hydrocarbon compound is substituted with a group capable of being substituted nucleophilically with a fluorine atom.

Examples of the optionally substituted aliphatic hydrocarbon compound include a C1-C20 unsubstituted aliphatic hydrocarbon compound such as methane, ethane, n-propane, isopropane, n-butane, isobutene, n-pentane, n-decane, cyclopropane, 2,2-dimethylcyclopropane, cyclopentane and cyclohexane, and these compounds of which at least one hydrogen atom is substituted with an uninvolved substituent in the reaction. Examples of the uninvolved substituent in the reaction include a fluorine atom; a C1-C20 alkoxy group which may be substituted with a fluorine atom or atoms such as a methoxy group, an ethoxy group, an n-propoxy group, an isopropoxy group, an n-butoxy group, an isobutoxy group, a sec-butoxy group, a tert-butoxy group and a trifluoromethoxy group; a C6-C20 aryl group which may be substituted with at least one selected from the group consisting of a fluorine atom, the above-mentioned alkoxy group and the C6-C20 aryloxy group described below such as a phenyl group, a 1-naphthyl group, a 2-naphthyl group, a 4-methylphenyl group, a 4-methoxyphenyl group, a 3-phenoxyphenyl group, a 2,3,5,6-tetrafluorophenyl group, a 2,3,5,6-tetrafluoro-4- methylphenyl group, a 2,3,5,6-tetrafluoro-4-methoxyphenyl group and a 2,3,5,6-tetrafluoro-4-methoxymethylphenyl group; a C5-C20 heteroaryl group which may be substituted with at least one selected from the group consisting of a fluorine atom and the above-mentioned alkoxy group such as a 2-pyridyl group; a C6-C20 aryloxy group which may be substituted with at least one selected from the group consisting of a fluorine atom, the above-mentioned alkoxy group and the C6-C20 aryloxy group such as a phenoxy group, a 2-methylphenoxy group, a 4-methylphenoxy group, a 4-methoxyphenoxy group and a 3-phenoxyphenoxy group; a C7-C20 aralkyloxy group which may be substituted with at least one selected from the group consisting of a fluorine atom, the above-mentioned alkoxy group and the above-mentioned aryloxy group such as a benzyloxy group, a 4-methylbenzyloxy group, a 4-methoxybenzyloxy group, a 3-phenoxybenzyloxy group, a 2,3,5,6-tetrafluorobenzyloxy group, a 2,3,5,6-tetrafluoro-4-methylbenzyloxy group, a 2,3,5,6-tetrafluoro-4-methoxybenzyloxy group and a 2,3,5,6-tetrafluoro-4-methoxymethylbenzyloxy group; a C2-C20 acyl group which may be substituted with at least one selected from the group consisting of a fluorine atom, the above-mentioned alkoxy group and the above-mentioned aryloxy group such as an acetyl group, a propionyl group, a benzoyl group, a 2-methylbenzoyl group, a 4-methylbenzoyl group, a 4-methoxybenzoyl group, a benzylcarbonyl group, a 4-methylbenzylcarbonyl group and a 4-methoxybenzylcarbonyl group; a carboxyl group; an aminosulfonyl group; a cyano group; and a carbamoyl group.

Examples of the aliphatic hydrocarbon compound substituted with the uninvolved substituent in the reaction include fluoromethane, trifluoromethane, methoxymethane, ethoxymethane, methoxyethane, toluene, 4-methoxybenzene, 3-phenoxybenzene, 2,3,5,6-tetrafluorotoluene, 2,3,5,6-tetrafluoro-4-methyltoluene, 2,3,5,6-tetrafluoro-4-methoxytoluene, 2,3,5,6-tetrafluoro-4-methoxymethyltoluene, 2-propyl-1-naphthalene, methyl isobutyl ketone, acetophenone, 4-methylacetophenone and phenylacetone.

Examples of the optionally substituted aromatic hydrocarbon compound include a C6-C20 unsubstituted aromatic hydrocarbon compound such as benzene, naphthalene and toluene, and these compounds of which at least one hydrogen atom is substituted with an uninvolved substituent in the reaction. Examples of the uninvolved substituent in the reaction include the same as described above. Alternatively, two neighboring substituents among these uninvolved substituents in the reaction may be bonded to form a ring together with the carbon atoms to which they are bonded.

Examples of the aromatic hydrocarbon compound substituted with the uninvolved substituent in the reaction include cyanobenzene, dicyanobenzene, fluorobenzene, difluorobenzene, benzenesulfonamide, biphenyl, 2-phenylnaphthalene, phenoxybenzene, benzophenone, 1,2-diphenylethanone and terephthalic acid.

Examples of the optionally substituted heteroaromatic hydrocarbon compound include a C5-C20 unsubstituted heteroaromatic hydrocarbon compound such as pyridine, methylpyridine, quinoline and pyrimidine, and these compounds of which at least one hydrogen atom is substituted with an uninvolved substituent in the reaction. Examples of the uninvolved substituent in the reaction include the same as described above. Alternatively, two neighboring substituents among these uninvolved substituents in the reaction may be bonded to form a ring together with the carbon atoms to which they are bonded.

Examples of the heteroaromatic hydrocarbon compound substituted with the uninvolved substituent in the reaction include 4-phenylpyridine and 3-methyl-5-trifluoromethylpyridine.

Specific examples of the organic compound include 1-chlorobutane, 1-bromobutane, 1-iodobutane, 1-chlorocyclobutane, 1-chloropentane, 1-bromopentane, 1-chlorocyclopentane, 1-chloro-4-bromobutane, 1-chlorohexane, 1-bromoheptane, 2-chloroheptane, 2-bromoheptane, 1-chlorooctane, 1-bromooctane, 2-chlorooctane, 2-bromooctane, benzyl chloride, benzyl bromide, (1-chloroethyl)benzene, (1-bromoethyl)benzene, 4-methoxybenzyl chloride, 4-methylbenzylbromide, 3,4,5-trifluorobenzylbromide, n-butyl p-toluenesulfonate, n-butyl methanesulfonate, n-pentyl p-toluenesulfonate, n-pentyl methanesulfonate, n-hexyl p-toluenesulfonate, n-hexyl methanesulfonate, n-heptyl p-toluenesulfonate, n-heptyl methanesulfonate, n-octyl p-toluenesulfonate, n-octyl methanesulfonate, n-butyl trifluoroacetate, n-butyl tetrafluorobenzoate, n-octyl trifluoroacetate, 4-chloronitrobenzene, 4-bromonitrobenzene, 2-chloronitrobenzene, 2-bromonitrobenzene, 2,4-dichloronitrobenzene, 2,6-dichloronitrobenzene, 3,5-dichloronitrobenzene, 4-cyanochlorobenzene, 4-cyanobromobenzene, 1-chloro-2,4-dinitrobenzene, tetrachloroterephthalonitrile, tetrachloroisophthalonitrile, tetrachloroorthophthalonitrile, 1,3-dichloro-4,6-dinitrobenzene, 2-chloroquinoline, 2-chloro-5-nitropyridine, 2-chloro-5-trifluoromethylpyridine and 4,5,6-trichloropyrimidine.

When the organic compound has two or more groups capable of being substituted nucleophilically with a fluorine atom, the fluorine-containing organic compound produced differs depending on the reaction conditions. Only the highest reactive substituent among groups capable of being substituted nucleophilically with a fluorine atom is sometimes substituted with a fluorine atom and all of the groups capable of being substituted nucleophilically with a fluorine atom are sometimes substituted with fluorine atoms.

When the organic compound wherein two or more groups capable of being substituted nucleophilically with a fluorine atom are bonded to the aromatic hydrocarbon group is used, the group capable of being substituted nucleophilically with a fluorine atom having a stronger electron-withdrawing group on para-or ortho-position is usually substituted preferentially with a fluorine atom. For example, when 4-chloronitrobenzene is used as the organic compound, the chlorine atom at 4-position having stronger electron-withdrawing nitro group on para-position is preferentially substituted with a fluorine atom and 4-fluoronitrobenzene is selectively produced. By selecting reaction conditions such as use of a large excess of the potassium fluoride dispersion, 1,4-difluorobenzene which the nitro group at 1-position can be also substituted with a fluorine atom as well as the chlorine atom at 4-position can be obtained.

When the organic compound wherein two or more groups capable of being substituted nucleophilically with a fluorine atom are bonded to the heteroaromatic hydrocarbon group is used, the group capable of being substituted nucleophilically with a fluorine atom on 2-, 4-or 6-position against the heteroatom composed of the heteroaromatic hydrocarbon group is usually substituted preferentially with a fluorine atom. For example, when 2-chloro-3-nitropyridine is used as the organic compound, the chlorine atom at 2-position against the nitrogen atom composed of the pyridyl group is preferentially substituted with a fluorine atom and 2-fluoro-3-nitropyridine is selectively produced. By selecting reaction conditions such as use of a large excess of the potassium fluoride dispersion, 2,3-Difluoropyridine which the nitro group at 3-position can be also substituted with a fluorine atom as well as the chlorine atom at 2-position can be obtained.

The amount of the potassium fluoride dispersion to be used may be decided arbitrarily depending on the number of the groups desired to substitute with a fluorine atom among groups capable of being substituted nucleophilically with a fluorine atom, and usually, the potassium fluoride containing 1 mole or more of potassium fluoride per 1 mole of the group desired to substitute with a fluorine atom is used. When the organic compound has one group desired to substitute with a fluorine atom, the potassium fluoride containing 1.5 to 5 moles of potassium fluoride per 1 mole of the organic compound is preferably used from the viewpoint of the reaction efficiency.

The contact of the potassium fluoride dispersion and the organic compound is usually conducted by mixing the both as it is or in the presence of a solvent. As the solvent, the above-mentioned aprotic polar solvent is preferable.

When the contacting temperature is too low, the fluorination reaction hardly proceeds and, when the contacting temperature is too high, side reaction such as degradation of the starting material or product may proceed. Therefore, the practical reaction temperature is 20 to 250° C.

The contact of the potassium fluoride dispersion and the organic compound may be carried out under normal pressure or under pressure.

The fluorination reaction of the organic compound proceeds by contacting the potassium fluoride dispersion with the organic compound, and the progress of the fluorination reaction can be checked by a conventional analytical means such as gas chromatography, high performance liquid chromatography, thin layer chromatography, NMR and IR.

After completion of the fluorination reaction, the fluorine-containing organic compound can be isolated, for example, by removing insoluble matters from the obtained reaction mixture by filtration followed by concentrating the obtained filtrate. Alternatively, the fluorine-containing organic compound can also be isolated by adding water and a solvent having a low compatibility with water to the reaction mixture to conduct extraction followed by concentrating the obtained organic layer. The fluorine-containing organic compound isolated may be further purified by a means such as distillation or column chromatography.

Examples of the solvent having a low compatibility with water include aromatic hydrocarbon solvents such as toluene, xylene and chlorobenzene; aliphatic hydrocarbon solvents such as pentane, hexane and heptane; halogenated hydrocarbon solvents such as dichloromethane, dichloroethane and chloroform; ether solvents such as diethyl ether, methyl tert-butyl ether and tetrahydrofuran; and ester solvents such as ethyl acetate.

Examples of the fluorine-containing organic compound thus obtained include 1-fluorobutane, 1-fluorocyclobutane, 1-fluoropentane, 1-fluorocyclopentane, 1,4-difluorobutane, 1-chloro-4-fluorobutane, 1-fluorohexane, 1,6-difluorohexane, 1-fluoroheptane, 2-fluoroheptane, 1-fluorooctane, 2-fluorooctane, benzyl fluoride, (1-fluoroethyl)benzene, 4-methoxybenzyl fluoride, 4-methylbenzyl fluoride, 3,4,5-trifluorobenzyl fluoride, 4-fluoronitrobenzene, 2-fluoronitrobenzene, 2,4-difluoronitrobenzene, 2,6-dichlorofluorobenzene, 3,5-difluoronitrobenzene, 4-cyanofluorobenzene, 1-fluoro-2,4-dinitrobenzene, tetrafluoroterephthalonitrile, tetrafluoroisophthalonitrile, tetrafluoroorthophthalonitrile, 1,3-difluoro-4,6-dinitrobenzene, 2-fluoroquinoline, 2-fluoro-5-nitropyridine, 2-fluoro-5-trifluoromethylpyridine, 4,6-difluoro-5-chloropyrimidine and 4,5,6-trifluoropyrimidine.

The fluorination reaction in which tetrachloroterephthaloyl dichloride is used as the organic compound will be illustrated below.

Tetrafluoroterephthaloyl difluoride can be produced by contacting tetrachloroterephthaloyl dichloride with the potassium fluoride dispersion.

Tetrachloroterephthaloyl dichloride can be produced, for example, according to a known method described in JP 2-11571 B or the like.

The amount of the potassium fluoride dispersion to be used may usually be the amount of the dispersion in which 6 moles or more of potassium fluoride per 1 mole of tetrachloroterephthaloyl dichloride is contained. While there is no specific upper limit, the amount of the dispersion in which 10 moles or less of potassium fluoride per 1 mole of tetrachloroterephthaloyl dichloride is contained is preferable from the economic viewpoint.

The potassium fluoride dispersion is preferably contacted with tetrachloroterephthaloyl dichloride at 120 to 200° C.

After completion of the reaction, tetrafluoroterephthaloyl difluoride can be isolated, for example, by concentrating the reaction mixture. Isolated tetrafluoroterephthaloyl difluoride may be further purified by a conventional purification means such as rectification.

Alternatively, the corresponding tetrafluoroterephthalic acid diester can be also produced by reacting obtained tetrafluoroterephthaloyl difluoride with an aliphatic alcohol compound.

Tetrafluoroterephthaloyl difluoride may be reacted with the aliphatic alcohol compound as it is without isolating from the above-mentioned reaction mixture.

Examples of the aliphatic alcohol compound include a C1-C6 aliphatic alcohol compound such as methanol, ethanol, n-propanol, isopropanol, n-butanol, tert-butanol and cyclohexanol.

The amount of the aliphatic alcohol compound to be used is not particularly limited. While the excess amount thereof may be used also to serve as the solvent, the practical amount thereof is 2 to 50 moles per 1 mole of tetrafluoroterephthaloyl difluoride.

The reaction of tetrafluoroterephthaloyl difluoride with the aliphatic alcohol compound is preferably carried out in the presence of an organic solvent. Examples of the organic solvent include aromatic hydrocarbon solvents such as toluene, xylene and chlorobenzene; aliphatic hydrocarbon solvents such as pentane, hexane and heptane; halogenated aliphatic hydrocarbon solvents such as dichloromethane, dichloroethane and chloroform; ether solvents such as diethyl ether and methyl tert-butyl ether; ester solvents such as ethyl acetate; and the above-mentioned aliphatic alcohol compounds. The amount of the organic solvent to be used is not particularly limited.

The reaction of tetrafluoroterephthaloyl difluoride with the aliphatic alcohol compound is usually conducted by mixing the both and the mixing order thereof is not particularly limited.

The reaction temperature is usually 0 to 100° C. While the reaction is usually carried out under normal pressure, the reaction may be conducted under pressure.

The progress of the reaction can be checked by a conventional analytical means such as gas chromatography and high performance liquid chromatography.

After completion of the reaction, the tetrafluoroterephthalic acid diester can be isolated by concentrating the reaction mixture, if necessary, after removing insoluble matters by filtration, followed by mixing the obtained concentrated residue with water to separate the precipitated solid by filtration. Alternatively, the tetrafluoroterephthalic acid diester can also be isolated by mixing the reaction mixture, water and as necessary, a solvent having a low compatibility with water to conduct extraction treatment followed by concentrating the obtained organic layer. Examples of the solvent having a low compatibility with water include aromatic hydrocarbon solvents such as toluene, xylene and chlorobenzene; aliphatic hydrocarbon solvents such as pentane, hexane and heptane; halogenated aliphatic hydrocarbon solvents such as dichloromethane, dichloroethane and chloroform; ether solvents such as diethyl ether and methyl tert-butyl ether; and ester solvents such as ethyl acetate. The amount thereof to be used is not particularly limited.

The tetrafluoroterephthalic acid diester isolated may be further purified by a conventional purification means such as crystallization and column chromatography.

Examples of the tetrafluoroterephthalic acid diester include dimethyl 2,3,5,6-tetrafluoroterephthalate, diethyl 2,3,5,6-tetrafluoroterephthalate, di(n-propyl) 2,3,5,6-tetrafluoroterephthalate, diisopropyl 2,3,5,6-tetrafluoroterephthalate, di(n-butyl) 2,3,5,6-tetrafluoroterephthalate and di(tert-butyl) 2,3,5,6-tetrafluoroterephthalate.

EXAMPLES

The present invention will be illustrated in more detail by Examples below. The present invention is not limited to these Examples.

Example 1

Into a 500 mL flask equipped with a reflux condenser, 30 g of potassium fluoride (purchased from NAKALAI TESQUE, INC.; commodity code 28611-95) and 400 g of methanol were charged. The obtained mixture was heated and refluxed for 30 minutes to prepare a methanol solution of potassium fluoride. To the obtained methanol solution of potassium fluoride, 100 g of toluene was added and the obtained mixture was concentrated at 90 to 100° C. to remove 200 g of a mixed solution of methanol and toluene. After 100 g of toluene was added to the concentrate, the obtained mixture was further concentrated at 90 to 100° C. to remove 200 g of a mixed solution of methanol and toluene. After 110 g of sulfolane was added to the obtained concentrate, the obtained mixture was concentrated at 130° C. to remove a mixed solution of methanol and toluene, and was further heated to 140° C. to continue the concentration until the distillate was hardly distilled at all. After that, residual toluene was removed by reducing to 6 kPa at 140° C. to obtain a potassium fluoride dispersion essentially consisting of potassium fluoride and sulfolane.

The potassium fluoride dispersion cooled at 100° C. was mixed with 22 g of tetrachloroterephthaloyl dichloride. The obtained mixture was kept for 3 hours at 145° C. with stirring. The obtained reaction mixture was cooled to 100° C. and then, 100 g of toluene was added thereto to cool to room temperature. A part of the obtained mixture was sampled to analyze with gas chromatography mass spectrometry apparatus. The formation of 2,3,5,6-tetrafluoroterephthaloyl difluoride as the main product and the disappearance of tetrachloroterephthaloyl dichloride were confirmed.

To the obtained reaction mixture, 15 g of methanol was added dropwise and the mixture was stirred for 12 hours at room temperature while removing hydrogen fluoride generated as by-product out the flask using nitrogen gas. The precipitated solid was separated by filtration and the separated solid was washed with 10 g of toluene. The filtrate and wash liquid were mixed and 100 g of water was added thereto and 300 mg of potassium carbonate was added thereto to adjust pH of the aqueous layer to 7. The obtained mixture was separated to an organic layer and an aqueous layer. The obtained organic layer was analyzed with gas chromatography internal standard method. The yield of dimethyl 2,3,5,6-tetrafluoroterephthalate was 88%, the yield of dimethyl 2,3,5-trifluoro-6-chloroterephthalate was 8% and the yield of dimethyl dichlorodifluoroterephthalate was 5%.

Example 2

Into a 200 mL flask equipped with a reflux condenser, 110 g of sulfolane was charged and the inner temperature thereof was adjusted at 140° C. To this, the solution obtained by dissolving 30 g of potassium fluoride, which was the same as used in Example 1, in 350 g of methanol was added dropwise together with removing distilled methanol out the system. The addition of all amount of the methanol solution of potassium fluoride dropwise was finished and methanol was hardly distilled out at all, and then, 50 g of toluene was added to the obtained concentrate. The concentration was continued at the same temperature to remove a mixed solution of methanol and toluene. After methanol was hardly distilled out, residual toluene was removed by reducing to 6 kPa to obtain a potassium fluoride dispersion essentially consisting of potassium fluoride and sulfolane.

The potassium fluoride dispersion cooled at 100° C. was mixed with 22 g of tetrachloroterephthaloyl dichloride. The obtained mixture was kept for 3.5 hours at 145° C. with stirring. The obtained reaction mixture was cooled to 100° C. and then, 100 g of toluene was added thereto. After the obtained mixture was cooled to room temperature, 15 g of methanol was added dropwise and the mixture was stirred for 12 hours at room temperature while removing hydrogen fluoride generated as by-product out the flask using nitrogen gas. The precipitated solid was separated by filtration and the separated solid was washed with 10 g of toluene. The filtrate and wash liquid were mixed and 100 g of water was added thereto and 400 mg of potassium carbonate was added thereto to adjust pH of the aqueous layer to 7. The obtained mixture was separated to an organic layer and an aqueous layer. The obtained organic layer was concentrated with an evaporator (operation pressure: 10 to 100 kPa, water bath temperature: 30 to 50° C.) to obtain the oily residue. The obtained residue was mixed with 110 g of water and then, the obtained mixture was further concentrated with an evaporator (operation pressure: 10 to 100 kPa, water bath temperature: 30 to 50° C.) to remove an azeotrope of toluene and water. The concentrated residue was cooled to room temperature and the precipitated crystals were separated by filtration. The obtained crystals were dried to obtain 17.2 g of pale yellow crystals of dimethyl 2,3,5,6-tetrafluoroterephthalate. The crystals were analyzed with gas chromatography area percentage method. The purity of dimethyl 2,3,5,6-tetrafluoroterephthalate was 93%. Yield: 93%.

Example 3

Into a 200 mL flask equipped with a reflux condenser, 110 g of sulfolane was charged and the inner temperature thereof was adjusted at 140° C. To this, the solution obtained by dissolving 30 g of potassium fluoride, which was the same as used in Example 1, in 350 g of methanol was added dropwise together with removing distilled methanol out the system. The addition of all amount of the methanol solution of potassium fluoride dropwise was finished and methanol was hardly distilled out at all, and then, the concentration was further continued at 160° C. at 2.7 kPa to obtain a potassium fluoride dispersion essentially consisting of potassium fluoride and sulfolane.

The potassium fluoride dispersion cooled at 100° C. was mixed with 22 g of tetrachloroterephthaloyl dichloride. The obtained mixture was kept for 3.5 hours at 145° C. with stirring. The obtained reaction mixture was cooled to 100° C. and then, 100 g of toluene was added thereto. After the obtained mixture was cooled to room temperature, 15 g of methanol was added dropwise to the cooled mixture and the resultant mixture was stirred for 12 hours at room temperature while removing hydrogen fluoride generated as by-product out the flask using nitrogen gas. The precipitated solid was separated by filtration and the separated solid was washed with 10 g of toluene. The filtrate and wash liquid were mixed and 100 g of water was added thereto and 600 mg of potassium carbonate was added thereto to adjust pH of the aqueous layer to 7. The obtained mixture was separated to an organic layer and an aqueous layer. The obtained organic layer was concentrated with an evaporator (operation pressure: 10 to 100 kPa, water bath temperature: 30 to 50° C.) to obtain the oily residue. The obtained residue was mixed with 110 g of water and then, the obtained mixture was further concentrated with an evaporator (operation pressure: 10 to 100 kPa, water bath temperature: 30 to 50° C.) to remove an azeotrope of toluene and water. The concentrated residue was cooled to room temperature and the precipitated crystals were separated by filtration. The obtained crystals were dried to obtain 17.4 g of pale yellow crystals of dimethyl 2,3,5,6-tetrafluoroterephthalate. The crystals were analyzed with gas chromatography area percentage method. The purity of dimethyl 2,3,5,6-tetrafluoroterephthalate was 92%. Yield: 93%.

Example 4

Into a 50 mL flask equipped with a reflux condenser, 480 mg of potassium fluoride, which was the same as used in Example 1, and 5 g of methanol were charged. The obtained mixture was heated and refluxed for 30 minutes to prepare a methanol solution of potassium fluoride. To the obtained methanol solution of potassium fluoride, 5 g of toluene was added and then, the obtained mixture was concentrated at 90 to 100° C. at normal pressure to remove a mixed solution of methanol and toluene. After methanol was hardly distilled at all, 1.7 g of dimethylsulfone was added to the concentrate. The obtained mixture was further concentrated at 140° C. to obtain a potassium fluoride dispersion essentially consisting of potassium fluoride and dimethylsulfone.

The potassium fluoride dispersion cooled at 100° C. was mixed with 340 mg of tetrachloroterephthaloyl dichloride. The obtained mixture was kept for 2 hours at 145° C. with stirring. The obtained reaction mixture was cooled to room temperature and then, 10 g of methanol was added. The solids in the obtained mixture were pulverized and then, the mixture was stirred at room temperature for 1 hour. To the mixture, 10 g of ethyl acetate was added and the resultant mixture was analyzed with gas chromatography internal standard method. The yield of dimethyl 2,3,5,6-tetrafluoroterephthalate was 75%, the yield of dimethyl 2,3,5-trifluoro-6-chloroterephthalate was 12% and the yield of dimethyl dichlorodifluoroterephthalate was 11%.

Comparative Example 1

Into a 50 mL flask equipped with a reflux condenser, 960 mg of potassium fluoride, which was the same as used in Example 1, and 2 g of methanol were charged. Although the obtained mixture was heated and refluxed for 30 minutes, potassium fluoride was not dissolved perfectly in methanol. To the obtained mixture, 3 g of sulfolane and 3 g of toluene were added and then, the obtained mixture was concentrated at 130° C. at normal pressure to remove a mixed solution of methanol and toluene. After methanol was hardly distilled at all, the mixture was further concentrated at 140° C. to obtain a potassium fluoride dispersion essentially consisting of potassium fluoride and sulfolane.

The potassium fluoride dispersion cooled at 100° C. was mixed with 680 mg of tetrachloroterephthaloyl dichloride. The obtained mixture was kept for 4 hours at 150° C. with stirring. The obtained reaction mixture was cooled to room temperature and then, 5 g of methanol was added. The resultant mixture was stirred at room temperature for 1 hour. To the obtained mixture, 10 g of ethyl acetate was added and the resultant mixture was analyzed with gas chromatography internal standard method. The yield of dimethyl 2-fluoro-3, 5,6-trichloroterephthalate was 1%, and the yield of dimethyl 2,3,5,6-tetrachloroterephthalate was 98%. The generation of dimethyl 2,3,5,6-tetrafluoroterephthalate, dimethyl 2,3,5-trifluoro-6-chloroterephthalate and dimethyl dichlorodifluoroterephthalate could not be confirmed.

Example 5

Into a 50 mL flask equipped with a reflux condenser, 25 g of sulfolane was charged and the inner temperature thereof was adjusted at 140° C. To this, the solution obtained by dissolving 4.5 g of potassium fluoride, which was the same as used in Example 1, in 60 g of methanol was added dropwise together with removing distilled methanol out the system. The addition of all amount of the methanol solution of potassium fluoride dropwise was finished and methanol was hardly distilled out at all, and then, 10 g of toluene was added to the concentrate. The concentration was further continued to remove a mixed solution of methanol and toluene. After that, residual toluene was removed by reducing to 6 kPa at the same temperature to obtain a potassium fluoride dispersion essentially consisting of potassium fluoride and sulfolane.

The potassium fluoride dispersion cooled at 100° C. was mixed with 5 g of 2,4-dichloronitrobenzene. The obtained mixture was kept for 10 hours at 180° C. with stirring. The obtained reaction mixture was cooled to 100° C. and then, 100 g of toluene was added thereto. The obtained mixture was cooled to room temperature.

The precipitated solid was separated by filtration and the separated solid was washed with 10 g of toluene. The filtrate and wash liquid were mixed and the obtained solution was analyzed with gas chromatography internal standard method. The yield of 2,4-difluoronitrobenzene was 92% and the yield of chlorofluoronitrobenzene was 8%.

Example 6

Into a 50 mL flask equipped with a reflux condenser, 25 g of sulfolane was charged and the inner temperature thereof was adjusted at 140° C. To this, the solution obtained by dissolving 4.5 g of potassium fluoride, which was the same as used in Example 1, in 60 g of methanol was added dropwise together with removing distilled methanol out the system. The addition of all amount of the methanol solution of potassium fluoride dropwise was finished and methanol was hardly distilled out at all, and then, the concentration was further conducted at 160° C. at 2.7 kPa to obtain a potassium fluoride dispersion essentially consisting of potassium fluoride and sulfolane. The potassium fluoride dispersion was analyzed with gas chromatography area comparison method. The amount of methanol was 0.02% by weight or less per 1 part by weight of sulfolane.

The potassium fluoride dispersion cooled at 100° C. was mixed with 5 g of 2,4-dichloronitrobenzene. The obtained mixture was kept for 8 hours at 180° C. with stirring. The obtained reaction mixture was cooled to 100° C. and then, 100 g of toluene was added thereto. The obtained mixture was cooled to room temperature. The precipitated solid was separated by filtration and the separated solid was washed with 10 g of toluene. The filtrate and wash liquid were mixed and the obtained solution was analyzed with gas chromatography internal standard method. The yield of 2,4-difluoronitrobenzene was 90% and the yield of chlorofluoronitrobenzene was 10%.

Example 7

Into a 50 mL flask equipped with a reflux condenser, 25 g of dimethylsulfoxide was charged and the inner temperature thereof was adjusted at 140° C. To this, the solution obtained by dissolving 2.8 g of potassium fluoride, which was the same as used in Example 1, in 40 g of methanol was added dropwise together with removing distilled methanol out the system. The addition of all amount of the methanol solution of potassium fluoride dropwise was finished and methanol was hardly distilled out at all, and then, residual methanol was removed together with 10 g of dimethylsulfoxide by reducing to 6 kPa to obtain a potassium fluoride dispersion essentially consisting of potassium fluoride and dimethylsulfoxide.

The potassium fluoride dispersion cooled at 100° C. was mixed with 5 g of 4-chloronitrobenzene. The obtained mixture was kept for 4 hours at 185° C. with stirring. The obtained reaction mixture was cooled to 100° C. and then, 100 g of toluene was added thereto. The obtained mixture was cooled to room temperature. The precipitated solid was separated by filtration and the separated solid was washed with 10 g of toluene. The filtrate and wash liquid were mixed and the obtained solution was analyzed with gas chromatography internal standard method. The yield of 4-fluoronitrobenzene was 97% and the recovery of 4-chloronitrobenzene was 3%.

Example 8

Into a 50 mL flask equipped with a reflux condenser, 25 g of N-methyl-2-pyrolidone was charged and the inner temperature thereof was adjusted at 140° C. To this, the solution obtained by dissolving 2.8 g of potassium fluoride, which was the same as used in Example 1, in 40 g of methanol was added dropwise together with removing distilled methanol out the system. The addition of all amount of the methanol solution of potassium fluoride dropwise was finished and methanol was hardly distilled out at all, and then, residual methanol was removed together with 10 g of N-methyl-2-pyrolidone by reducing to 6 kPa to obtain a potassium fluoride dispersion essentially consisting of potassium fluoride and N-methyl-2-pyrolidone.

The potassium fluoride dispersion cooled at 100° C. was mixed with 5.5 g of benzyl bromide. The obtained mixture was kept for 4 hours at 120° C. with stirring. The obtained reaction mixture was cooled to 100° C. and then, 100 g of toluene was added thereto. The obtained mixture was cooled to room temperature. The precipitated solid was separated by filtration and the separated solid was washed with 10 g of toluene. The filtrate and wash liquid were mixed and the obtained solution was analyzed with gas chromatography internal standard method. The yield of benzyl fluoride was 93% and the recovery of benzyl bromide was 3%.

Example 9

Into a 500 mL flask, 350 g of methanol and 29 g of potassium hydroxide were charged. The mixture was stirred at room temperature to prepare a methanol solution of potassium hydroxide. To the prepared methanol solution of potassium hydroxide, 22 g of 47% by weight hydrofluoric acid was added dropwise while cooling to keep at an inner temperature of 30° C. or less to prepare a potassium fluoride solution.

Into a 200 mL flask equipped with a reflux condenser, 110 g of sulfolane was charged and the inner temperature thereof was adjusted at 140° C. To this, the above-mentioned potassium fluoride solution was added dropwise together with removing distilled mixed solution of methanol and water. The addition of all amount of the potassium fluoride solution dropwise was finished and methanol and water were hardly distilled out at all, and then, 10 g of toluene was added thereto. The concentration was further continued to remove a mixed solution of methanol, water and toluene. After the distillate was hardly distilled out, residual toluene was removed at the same temperature by reducing to 6 kPa to obtain a potassium fluoride dispersion essentially consisting of potassium fluoride and sulfolane.

The potassium fluoride dispersion cooled at 100° C. was mixed with 22 g of tetrachloroterephthaloyl dichloride. The obtained mixture was kept for 4 hours at 145° C. with stirring. The obtained reaction mixture was cooled to 100° C. and then, 100 g of toluene was added thereto and the obtained mixture was cooled to room temperature. To the obtained mixture, 15 g of methanol was added dropwise and the mixture was stirred for 12 hours at room temperature while removing hydrogen fluoride generated as by-product out the flask using nitrogen gas. The precipitated solid was separated by filtration and the separated solid was washed with 10 g of toluene. The filtrate and wash liquid were mixed and 100 g of water was added thereto and 600 mg of potassium carbonate was added thereto to adjust pH of the aqueous layer to 7. The obtained mixture was separated to an organic layer and an aqueous layer. The obtained organic layer was concentrated with an evaporator (operation pressure: 10 to 100 kPa, water bath temperature: 30 to 50° C.) to obtain the oily residue. The obtained residue was mixed with 110 g of water and then, the obtained mixture was further concentrated with an evaporator (operation pressure: 10 to 100 kPa, water bath temperature: 30 to 50° C.) to remove an azeotrope of toluene and water. The concentrated residue was cooled to room temperature and the precipitated crystals were separated by filtration. The obtained crystals were dried to obtain 17.6 g of pale yellow crystals of dimethyl 2,3,5,6-tetrafluoroterephthalate. The crystals were analyzed with gas chromatography area percentage method. The purity of dimethyl 2,3,5,6-tetrafluoroterephthalate was 87%. Yield: 89%.

Example 10

Into a 200 mL flask, 53 g of methanol and 4.4 g of potassium hydroxide were charged. The mixture was stirred at room temperature to prepare a methanol solution of potassium hydroxide. To the prepared methanol solution of potassium hydroxide, 3.3 g of 47% by weight hydrofluoric acid was added dropwise while cooling to keep at an inner temperature of 30° C. or less to prepare a potassium fluoride solution.

Into a 50 mL flask equipped with a reflux condenser, 25 g of sulfolane was charged and the inner temperature thereof was adjusted at 140° C. To this, the above-mentioned potassium fluoride solution was added dropwise together with removing distilled mixed solution of methanol and water out the system. The addition of all amount of the potassium fluoride solution dropwise was finished and methanol and water were hardly distilled out at all, and then, the concentration was continued at 160° C. at 2.7 kPa to remove residual methanol and water to obtain a potassium fluoride dispersion essentially consisting of potassium fluoride and sulfolane.

The potassium fluoride dispersion cooled at 100° C. was mixed with 5 g of 2,4-dichloronitrobenzene. The obtained mixture was kept for 10 hours at 180° C. with stirring. The obtained reaction mixture was cooled to 100° C. and then, 100 g of toluene was added thereto and the obtained mixture was cooled to room temperature. The precipitated solid was separated by filtration and the separated solid was washed with 10 g of toluene. The filtrate and wash liquid were mixed to analyze with gas chromatography internal standard method. The Yield of 2,4-difluoronitrobenzene was 89% and the yield of chlorofluoronitrobenzene was 9%.

Example 11

Into a 200 mL flask, 35 g of methanol and 2.7 g of potassium hydroxide were charged. The mixture was stirred at room temperature to prepare a methanol solution of potassium hydroxide. To the prepared methanol solution of potassium hydroxide, 2 g of 47% by weight hydrofluoric acid was added dropwise while cooling to keep at an inner temperature of 30° C. or less to prepare a potassium fluoride solution.

Into a 50 mL flask equipped with a reflux condenser, 25 g of N-methyl-2-pyrolidone was charged and the inner temperature thereof was adjusted at 140° C. To this, the above-mentioned potassium fluoride solution was added dropwise together with removing distilled a mixed solution of methanol and water out the system. The addition of all amount of the potassium fluoride solution dropwise was finished and methanol and water were hardly distilled out at all, and then, residual methanol and water were removed together with 10 g of N-methyl-2-pyrolidone by reducing to 6 kPa to obtain a potassium fluoride dispersion essentially consisting of potassium fluoride and N-methyl-2-pyrolidone.

The potassium fluoride dispersion cooled at 100° C. was mixed with 5.5 g of benzyl bromide. The obtained mixture was kept for 4 hours at 120° C. with stirring. The obtained reaction mixture was cooled to 100° C. and then, 100 g of toluene was added thereto. The obtained mixture was cooled to room temperature. The precipitated solid was separated by filtration and the separated solid was washed with 10 g of toluene. The filtrate and wash liquid were mixed and the obtained solution was analyzed with gas chromatography internal standard method. The yield of benzyl fluoride was 94% and the recovery of benzyl bromide was 3%.

Example 12

Into a 500 mL flask equipped with a reflux condenser, 75 g of sulfolane was charged and the inner temperature thereof was adjusted at 140° C. To this, the solution obtained by dissolving 17.8 g of potassium fluoride, which was the same as used in Example 1, in 209 g of methanol was added dropwise together with removing distilled methanol out the system. The addition of all amount of the methanol solution of potassium fluoride dropwise was finished and methanol hardly distilled out at all, and then, the concentration was further conducted at 160° C. at 2.7 kPa to obtain a potassium fluoride dispersion essentially consisting of potassium fluoride and sulfolane.

To a 120 mL nautoclave, 10.3 g of 4,5,6-trichloropyrimidine was charged. The above-mentioned potassium fluoride dispersion was added thereto and the autoclave was sealed. After the inner pressure thereof was adjusted to 0.5 MPa at room temperature using nitrogen, the reaction was conducted at an inner temperature of 220° C. for 10 hours. The inner pressure after completion of the reaction was 0.82 MPa at 220° C. The reaction mixture was cooled to room temperature and the supernatant solution was analyzed with gas chromatography internal standard method (internal standard: methyl isobutyl ketone). The yield of 4,5,6-trifluoropyrimidine was 50% and the yield of 4,6-difluoro-5-chloropyrimidine was 26%.

Example 13

Into a 200 mL flask equipped with a reflux condenser, 70 g of sulfolane was charged and the inner temperature thereof was adjusted at 140° C. To this, the solution obtained by dissolving 13.6 g of potassium fluoride (purchased from ALDRICH; spray-dry products; commodity code 307599) and 1.0 g of water in 180 g of methanol was added dropwise together with removing distilled a mixed solution of methanol and water out the system. The addition of all amount of the potassium fluoride solution dropwise was finished and methanol was hardly distilled out at all, and then, the concentration was further conducted at 160° C. at 2.7 kPa to obtain a potassium fluoride dispersion essentially consisting of potassium fluoride and sulfolane.

The potassium fluoride dispersion cooled at 140° C. was mixed with 10 g of tetrachloroterephthaloyl dichloride. The obtained mixture was kept for 3 hours at 145° C. with stirring. The obtained reaction mixture was cooled to 100° C. and then, 20 g of toluene was added thereto. The obtained mixture was cooled to room temperature. To the obtained mixture, 9.4 g of methanol was added dropwise and the mixture was stirred for 1 hour at room temperature while removing hydrogen fluoride generated as by-product out the flask using nitrogen gas out the flask. The precipitated solid was separated by filtration and the separated solid was washed with 50 g of toluene. The filtrate and wash liquid were mixed and the obtained solution was analyzed with gas chromatography internal standard method. The yield of dimethyl 2,3,5,6-tetrafluoroterephthalate was 82%, the yield of dimethyl 2,3,5-trifluoro-6-chloroterephthalate was 7% and the yield of dimethyl dichlorodifluoroterephthalate was 5%.

Comparative Example 2

Into a 200 mL flask equipped with a reflux condenser, 13.6 g of potassium fluoride, which was the same as used in the above-mentioned Example 13, 1.0 g of water and 20 g of methanol were charged. Although the obtained mixture was refluxed for 30 minutes, potassium fluoride was not dissolved perfectly to obtain suspension of potassium fluoride. To the obtained suspension of potassium fluoride, 70 g of sulfolane and 22 g of toluene were added and then, the obtained mixture was concentrated at an inner temperature of 130° C. to remove a mixed solution of methanol, water and toluene out the system. After methanol was hardly distilled at all, the mixture was further concentrated at 140° C. to obtain a potassium fluoride dispersion essentially consisting of potassium fluoride and sulfolane. The potassium fluoride dispersion cooled at 140° C. was mixed with 10 g of tetrachloroterephthaloyl dichloride. The obtained mixture was kept for 3 hours at 145° C. with stirring. The obtained reaction mixture was cooled to 100° C. and then, 20 g of toluene was added thereto. The obtained mixture was cooled to room temperature. To the obtained mixture, 9.4 g of methanol was added dropwise and the mixture was stirred for 1 hour at room temperature while removing hydrogen fluoride generated as by-product out the flask using nitrogen gas out the flask. The precipitated solid was separated by filtration and the separated solid was washed with 50 g of toluene. The filtrate and wash liquid were mixed and the obtained solution was analyzed with gas chromatography internal standard method. The yield of dimethyl 2,3,5,6-tetrafluoroterephthalate was 1%, the yield of dimethyl 2,3,5-trifluoro-6-chloroterephthalate was 10%, the yield of dimethyl dichlorodifluoroterephthalate was 8%, the yield of dimethyl 2-fluoro-3,5,6-trichloroterephthalate was 10% and the yield of 2,3,5,6-tetrachloroterephthalate was 4%.

Example 14

Into a 500 mL flask equipped with a reflux condenser, 300 g of sulfolane was charged and the inner temperature thereof was adjusted at 140° C. To this, the solution obtained by dissolving 58 g of potassium fluoride, which was the same as used in the above-mentioned Example 13, 3 g of water in 772 g of methanol was added dropwise together with removing distilled mixed solution of methanol and water out the system. The addition of all amount of the potassium fluoride solution dropwise was finished and methanol was hardly distilled out at all, and then, the concentration was further conducted at 160° C. at 2.7 kPa to obtain a potassium fluoride dispersion essentially consisting of potassium fluoride and sulfolane. The number of particles and the volumetric particle size distribution of potassium fluoride in the obtained potassium fluoride dispersion were measured using the FBRM "D600L" to get particle size distribution data using a data-processing system with "D600L". The obtained volumetric particle size distribution data was shown in FIG. 1. The average particle size of volumetric was 19.7 μm.

Figure 5:
FIG. 5 This is an image of FE-SEM of potassium fluoride particles in the potassium fluoride dispersion obtained in Example 14 (2,000-fold magnification for shooting).
Figure 6:
FIG. 6 This is an image of FE-SEM of potassium fluoride particles in the potassium fluoride dispersion obtained in Example 14 (5,000-fold magnification for shooting).

After completion of the measurement, the potassium fluoride dispersion was filtrated and the obtained particles of potassium fluoride was washed with 100 g of ethyl acetate and dried at 80° C. at 1.3 kPa. The dried particles of potassium fluoride was subjected to the pretreatment by Pt—Pd evaporation method and form observation was conducted under 10 kV of accelerating voltage using FE-SEM "S-800" manufactured by HITACHI, Ltd. to confirm that the particle diameter of the initial particles of potassium fluoride was 0.1 to 5 μm. The results were shown in FIG. 5 and FIG. 6. FIG. 5 was a SEM image at 2,000-fold magnification for shooting and FIG. 6 was a SEM image at 5,000-fold magnification for shooting.

Comparative Example 3

Figure 2:
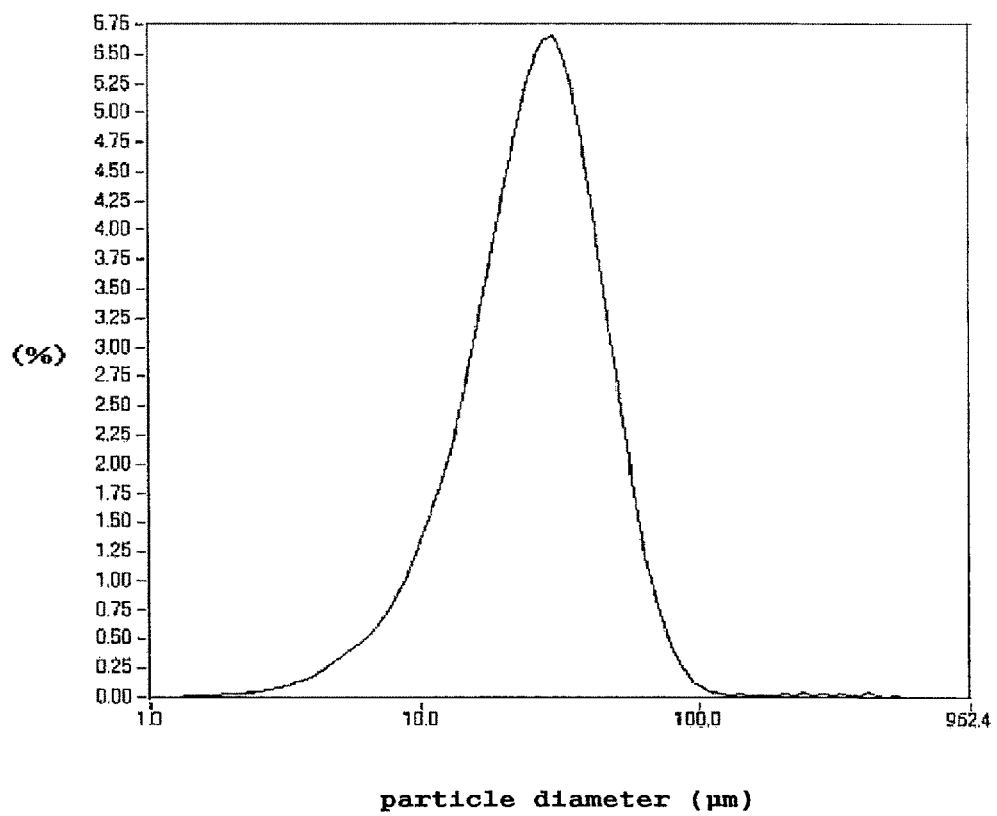
FIG. 2 This is a drawing showing volumetric particle size distribution of the potassium fluoride dispersion obtained in Comparative Example 3.

Into a 500 mL flask equipped with a reflux condenser, 83 g of potassium fluoride, which was the same as used in the above-mentioned Example 13, 5 g of water and 119 g of methanol were charged. Although the obtained mixture was refluxed for 30 minutes, potassium fluoride was not dissolved perfectly to obtain suspension of potassium fluoride. To the obtained suspension of potassium fluoride, 300 g of sulfolane and 130 g of toluene were added and then, the obtained mixture was concentrated at an inner temperature of 130° C. to remove a mixed solution of methanol, water and toluene out the system. After methanol was hardly distilled at all, the mixture was further concentrated at 140° C. to obtain a potassium fluoride dispersion essentially consisting of potassium fluoride and sulfolane. The number of particles and the volumetric particle size distribution of potassium fluoride in the obtained potassium fluoride dispersion were measured using the FBRM "D600L" to get particle size distribution data using a data-processing system with "D600L". The obtained volumetric particle size distribution data was shown in FIG. 2. The average particle size of volumetric was 29.7 μm.

Figure 7:
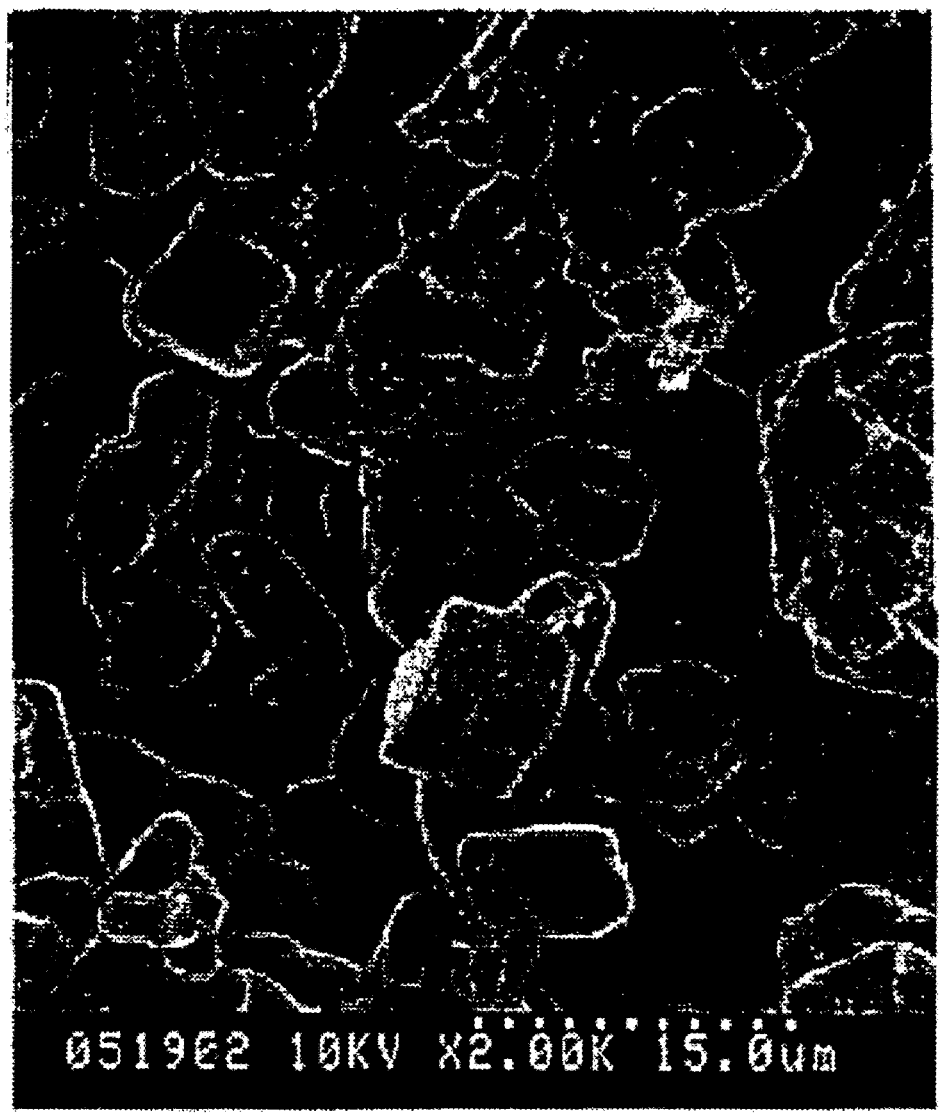
FIG. 7 This is an image of FE-SEM of potassium fluoride particles in the potassium fluoride dispersion obtained in Comparative Example 3 (2,000-fold magnification for shooting).

After completion of the measurement, the potassium fluoride dispersion was filtrated and the obtained particles of potassium fluoride was washed with 150 g of ethyl acetate and dried at 80° C. at 1.3 kPa. The dried particles of potassium fluoride was subjected to the pretreatment by Pt—Pd evaporation method and form observation was conducted under 10 kV of accelerating voltage using FE-SEM "S-800" manufactured by HITACHI, Ltd. The result was shown in FIG. 7. FIG. 7 was a SEM image at 2,000-fold magnification for shooting.

Comparative Example 4

Figure 3:
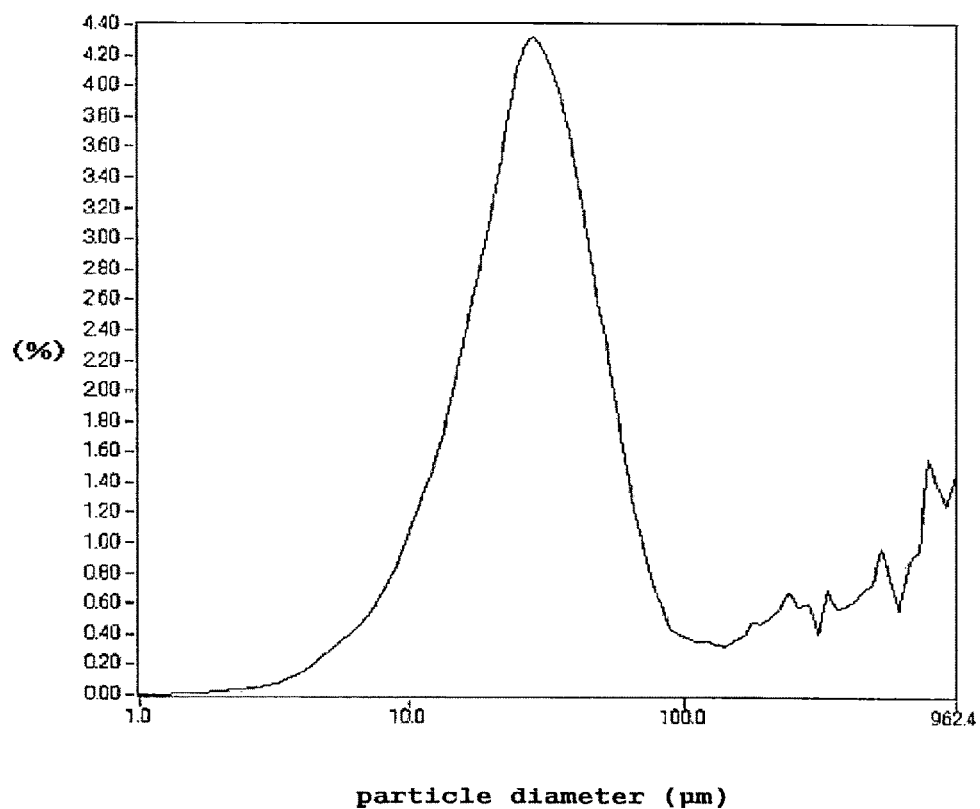
FIG. 3 This is a drawing showing volumetric particle size distribution of the potassium fluoride dispersion obtained in Comparative Example 4.

Potassium fluoride, which was the same as used in the above-mentioned Example 13, was dispersed in sulfolane to prepare a potassium fluoride dispersion. The number of particles and the volumetric particle size distribution of potassium fluoride in the obtained potassium fluoride dispersion were measured using the FBRM "D600L" to get particle size distribution data using a data-processing system with "D600L". The obtained volumetric particle size distribution data was shown in FIG. 3. The average particle size of volumetric was 127.2 μm.

Figure 8:
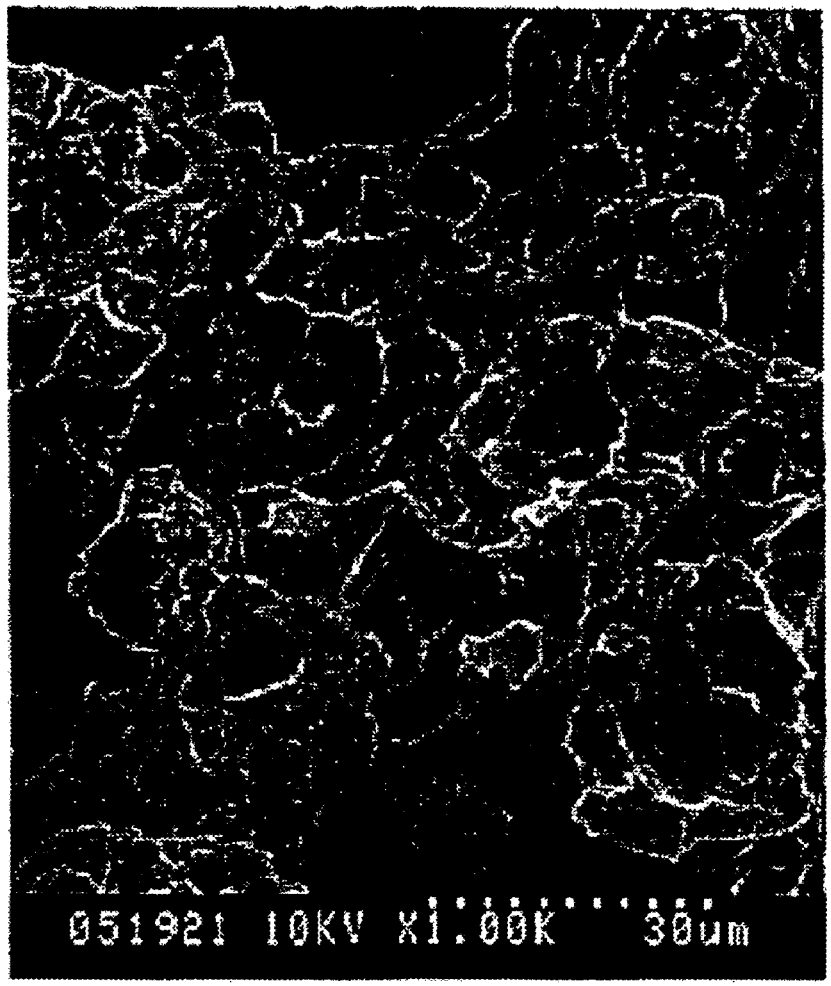
FIG. 8 This is an image of FE-SEM of potassium fluoride particles in the potassium fluoride dispersion obtained in Comparative Example 4 (1,000-fold magnification for shooting).

After completion of the measurement, the potassium fluoride dispersion was filtrated and the obtained particles of potassium fluoride was washed with 150 g of ethyl acetate and dried at 80° C. at 1.3 kPa. The dried particles of potassium fluoride was subjected to the pretreatment by Pt—Pd evaporation method and form observation was conducted under 10 kV of accelerating voltage using FE-SEM "S-800" manufactured by HITACHI, Ltd. The result was shown in FIG. 8. FIG. 8 was a SEM image at 1,000-fold magnification for shooting.

Example 15

Figure 4:
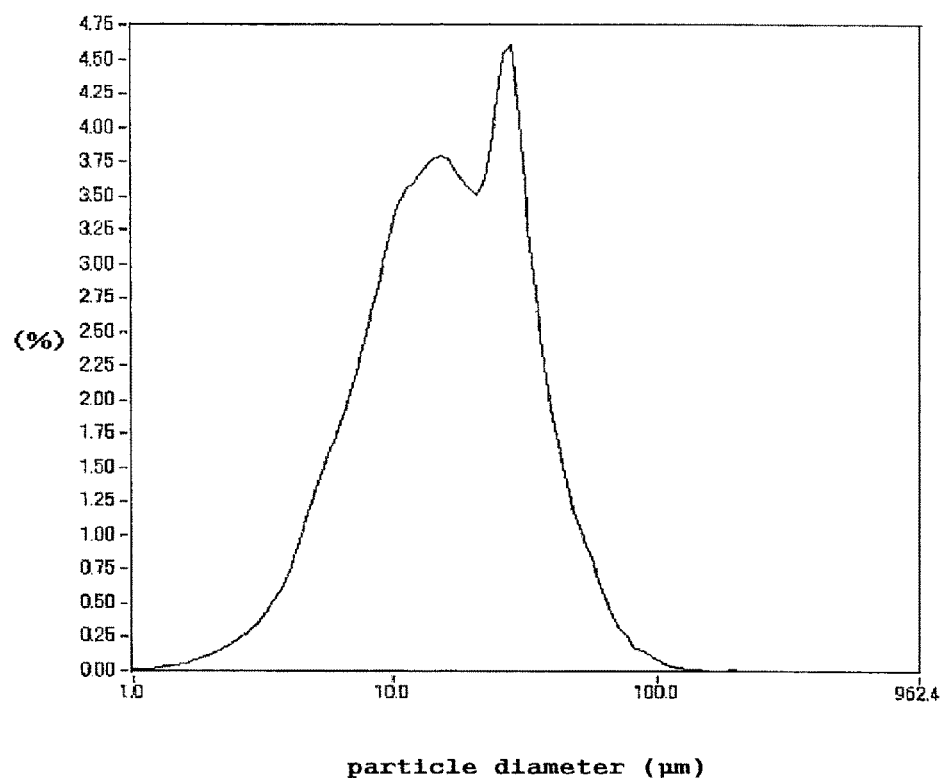
FIG. 4 This is a drawing showing volumetric particle size distribution of the potassium fluoride dispersion obtained in Example 15.

Into a 500 mL flask equipped with a reflux condenser, 300 g of sulfolane was charged and the inner temperature thereof was adjusted at 140° C. To this, the solution obtained by dissolving 58 g of potassium fluoride, which was the same as used in the above-mentioned Example 1, in 772 g of methanol was added dropwise together with removing distilled methanol out the system. The addition of all amount of the potassium fluoride solution dropwise was finished and methanol was hardly distilled out at all, and then, the concentration was further conducted at 160° C. at 2.7 kPa to obtain a potassium fluoride dispersion essentially consisting of potassium fluoride and sulfolane. The number of particles and the volumetric particle size distribution of potassium fluoride in the obtained potassium fluoride dispersion were measured using the FBRM "D600L" to get particle size distribution data using a data-processing system with "D600L". The obtained volumetric particle size distribution data was shown in FIG. 4. The average particle size of volumetric was 20.2 μm.

Figure 9:
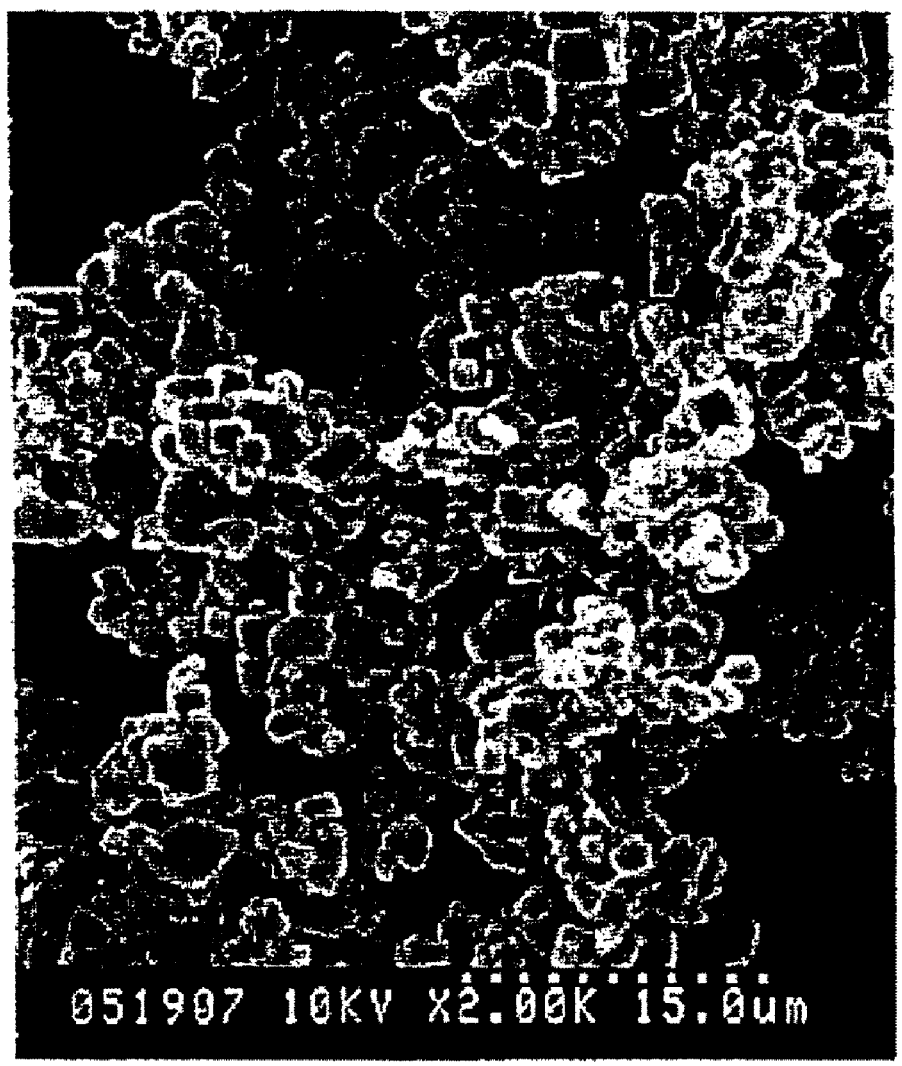
FIG. 9 This is an image of FE-SEM of potassium fluoride particles in the potassium fluoride dispersion obtained in Example 15 (2,000-fold magnification for shooting).
Figure 10:
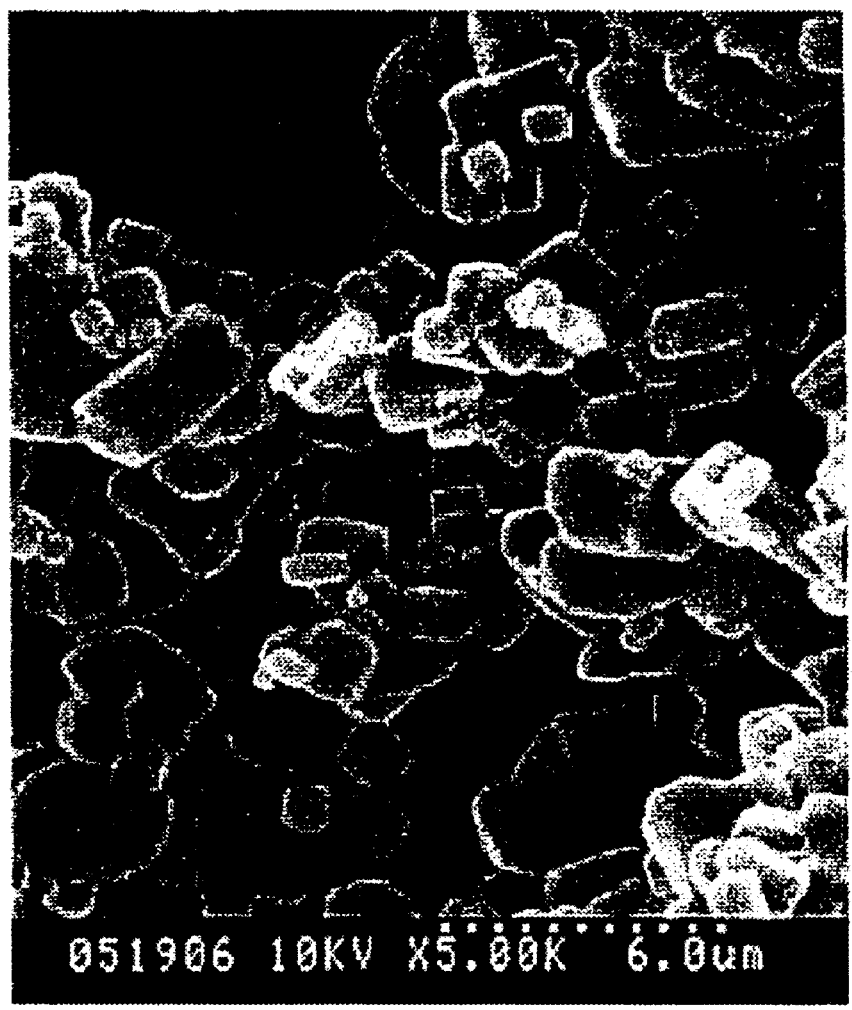
FIG. 10 This is an image of FE-SEM of potassium fluoride particles in the potassium fluoride dispersion obtained in Example 15 (5,000-fold magnification for shooting).

After completion of the measurement, the potassium fluoride dispersion was filtrated and the obtained particles of potassium fluoride was washed with 100 g of ethyl acetate and dried at 80° C. at 1.3 kPa. The dried particles of potassium fluoride was subjected to the pretreatment by Pt—Pd evaporation method and form observation was conducted under 10 kV of accelerating voltage using FE-SEM "S-800" manufactured by HITACHI, Ltd. to confirm that the particle diameter of the initial particles of potassium fluoride was 0.1 to 5 µm. The results were shown in FIG. 9 and FIG. 10. FIG. 9 was a SEM image at 2,000-fold magnification for shooting and FIG. 10 was a SEM image at 5,000-fold magnification for shooting.

Industrial Applicability

The potassium fluoride dispersion of the present invention has high reactivity and fluorine-containing organic compounds, which are important as various chemicals such as pharmaceuticals and agrichemicals and its synthetic intermediates, can be produced efficiently without using an expensive phase transfer catalyst, and therefore, it is industrially advantageous.

The invention claimed is:

1. A process for producing a potassium fluoride dispersion, comprising:
preparing a mixture containing potassium fluoride and 5 to 50 parts by weight of methanol per 1 part by weight of potassium fluoride with an aprotic organic solvent having a boiling point higher than that of methanol followed by concentrating the obtained mixture to obtain a potassium fluoride dispersion consisting essentially of the potassium fluoride and the aprotic organic solvent having a boiling point higher than that of methanol, wherein the mixture being a solution wherein potassium fluoride is dissolved completely in the methanol,
wherein a part or all of initial particles of the potassium fluoride in the dispersion, which have a particle diameter of 0.1 to 5 µm, are flocculated to form particles having 5 to 25 µm of volumetric average particle diameter, and the aprotic organic solvent is selected from the group consisting of ether solvents, sulfone solvents, sulfoxide solvents, amide solvents, nitrile solvents and mixtures thereof.

2. The process of claim 1, wherein the aprotic organic solvent having a boiling point higher than that of methanol is selected from the group consisting of diisopropyl ether, dibutyl ether, dioxane, diethylene glycol dimethyl ether, triethylene glycol dimethyl ether, sulfolane, dimethylsulfone, methyl ethyl sulfone, dimethylsulfoxide, diethylsulfoxide, tetramethylenesulfoxide, N,N-dimethylformamide, N,N-dimethylacetamide, N-methylpyrolidone, butyronitrile, adiponitrile and mixtures thereof.

3. The process of claim 1, wherein the concentrating is conducted while adding the mixture containing potassium fluoride and 5 to 50 parts by weight of methanol per 1 part by weight of potassium fluoride into the aprotic organic solvent having a boiling point higher than that of methanol, which is adjusted at a temperature which is the boiling point of methanol or more.

4. The process of claim 1, wherein aprotic organic solvent having a boiling point higher than that of methanol is an aprotic polar solvent.

5. The process of claim 4, wherein the aprotic polar solvent is a sulfone solvent or a sulfoxide solvent.

6. The process of claim 1, wherein the mixture contains potassium fluoride and 8 to 50 parts by weight of methanol per 1 part by weight of potassium fluoride.

7. The process of claim 1, wherein the mixture contains 1 part per weight or more of the aprotic organic solvent per 1 part by weight of the potassium fluoride.

8. The process of claim 1, wherein the mixture contains 1 to 20 parts per weight of the aprotic organic solvent per 1 part by weight of the potassium fluoride.

* * * * *